(12) United States Patent
Shirai

(10) Patent No.: US 6,623,612 B2
(45) Date of Patent: Sep. 23, 2003

(54) SEALING STRUCTURE OF GAS SENSOR

(75) Inventor: Makoto Shirai, Hekinan (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/877,205

(22) Filed: Jun. 11, 2001

(65) Prior Publication Data

US 2002/0000375 A1 Jan. 3, 2002

(30) Foreign Application Priority Data

| | | | |
|---|---|---|---|
| Jun. 30, 2000 | (JP) | | 2000-197998 |
| Jun. 30, 2000 | (JP) | | 2000-197999 |
| Mar. 26, 2001 | (JP) | | 2001-088347 |
| Feb. 23, 2001 | (JP) | | 2001-049086 |

(51) Int. Cl.⁷ ......................................... G01N 27/407
(52) U.S. Cl. .................... 204/424; 204/427; 204/428
(58) Field of Search ................. 204/421–429

(56) References Cited

U.S. PATENT DOCUMENTS

| | | | |
|---|---|---|---|
| 4,057,477 A | * | 11/1977 | Weyl et al. |
| 4,123,344 A | * | 10/1978 | Davis |
| 4,339,320 A | * | 7/1982 | Friese et al. |
| 5,707,504 A | * | 1/1998 | Jyouno et al. |
| 5,795,454 A | | 8/1998 | Friese et al. |
| 5,874,664 A | | 2/1999 | Watanabe et al. |
| 5,942,092 A | * | 8/1999 | Weyl et al. |
| 6,096,181 A | * | 8/2000 | Friese et al. |

FOREIGN PATENT DOCUMENTS

| | | |
|---|---|---|
| DE | 19707456 A1 | 8/1998 |
| EP | 1004876 A2 | 5/2000 |
| JP | 8-511098 | 11/1996 |
| WO | WO 98/15820 | 4/1998 |

* cited by examiner

*Primary Examiner*—T. Tung
(74) *Attorney, Agent, or Firm*—Nixon & Vanderhye P.C.

(57) ABSTRACT

An improved structure of a mechanical seal for keeping a gas chamber and a reference gas chamber airtight in a sensor body. A packing seal is disposed between a shoulder formed on an inner wall of a housing of the sensor body and a tapered surface of an insulation porcelain installed in the housing to define the gas chamber and the reference gas chamber hermetically. The packing ring is formed by a metal plate which has a thickness of 0.1 mm or more and a Vickers hardness of 200 or less and which is made of at least one of a nickel, a nickel alloy, a titanium, and a stainless steel.

16 Claims, 5 Drawing Sheets

SEALING STRUCTURE OF GAS SENSOR

BACKGROUND OF THE INVENTION

1. Technical Field of the Invention

The present invention relates generally to a gas sensor which may be installed in an exhaust system of an internal combustion engine for air-fuel ratio control, and more particularly to an improved structure of a mechanical seal which keeps a reference gas chamber and a gas chamber airtight in a gas sensor.

2. Background Art

Gas sensors are known which are fabricated by inserting a sensor element into an insulation porcelain, mounting the insulation porcelain in a housing, installing a gas cover and an air cover on a front end and a base end of the housing, respectively, and sealing the gap between the insulation porcelain and the housing hermetically. This seal defines a measured gas chamber and an air chamber within the gas sensor.

The sensor element has a measuring electrode exposed to a gas to be measured and a reference electrode exposed to a reference gas or air and provides a signal in the form of an ion current flowing through the measuring and reference electrodes or a potential difference between the measuring and reference electrodes to determine the concentration of the gas. The leakage of the gas from the measured gas chamber to the air chamber will, thus, result in a decrease in accuracy of measuring the concentration of the gas. In order to avoid this problem, typical gas sensors pack powder material such as talc in the gap between the insulation porcelain and the housing to separate the measured gas chamber and the air chamber hermetically.

The use of powder material such as talc, however, results in an economical disadvantage that the pressure required to pack the powder material and the amount of powder material must be controlled finely and precisely.

In order to alleviate such a drawback, bulk material-made packing is proposed as a sealing member. For example, U.S. Pat. No. 5,795,454 teaches a ceramic ring baked at lower temperature for sealing a gap between a sensor element and a housing to define a measured gas chamber and a reference gas chamber hermetically. The ceramic ring, however, usually remains having a certain degree of porosity even after the ceramic ring is installed under high pressure, which may result in lack of airtightness between the sensor element and the housing.

U.S. Pat. No. 5,795,454 also discloses use of a lower porosity metallic ring together with the ceramic ring for increasing the degree of the airtightness, however, it will result in increases in fabrication process and manufacturing cost. Moreover, the metallic ring may corrode early depending upon the type of a gas to be measured, which leads to a decrease in degree of the airtightness between the measured gas chamber and the reference gas chamber.

U.S. Pat. No. 5,795,454 further discloses a metal seal coated with nickel or copper, however, it requires plating or cladding the whole surface of the metal seal, thus resulting in an increase in manufacturing cost.

SUMMARY OF THE INVENTION

It is therefore a principal object of the invention to avoid the disadvantages of the prior art.

It is another object of the invention to provide an improved structure of a gas sensor which provides a mechanical seal required to keep a reference gas chamber and a gas chamber in the gas sensor airtight highly.

According to the first aspect of the invention, there is provided a gas sensor which features a mechanical seal and which may be installed in an exhaust system of an internal combustion engine for air-fuel ratio control. The gas sensor comprises: (a) a hollow housing having a sealing shoulder formed on an inner wall thereof; (b) a sensor element having a length which includes a first and a second portion; (c) an insulating member disposed within the housing, retaining the sensor element therein hermetically, the insulating member having a sealing surface formed thereon; and (d) a metal sealing member interposed between the sealing shoulder of the housing and the sealing surface of the insulating member to hermetically define a first chamber in which the first portion of the sensor element is disposed and a second chamber in which the second portion of the sensor element is disposed. The metal sealing member is made of at least one of a nickel, a nickel alloy, a titanium, and a stainless steel.

In the preferred mode of the invention, the first chamber leads to the atmosphere. The second chamber is so constructed as to admit a gas to be measured thereinto.

An air cover is installed on an end of the housing to define the first chamber therein.

The metal sealing member has a Vickers hardness of 200 or less and a thickness of 0.1 mm or more.

The metal sealing member may be made up of a first layer and a second layer. The first layer is in contact with the sealing shoulder of the housing. The second layer is in contact with the sealing surface of the insulating member and has a hardness lower than that of the first layer. The second layer has a Vickers hardness of 200 or less.

The sealing surface of the insulating member is tapered. The sealing shoulder of the housing is so oriented as to adhere to the sealing surface of the insulating member through the metal sealing member.

The insulating member is made of an alumina ceramic having an alumina purity of 90% or more.

The sealing surface of the insulating member has a ten-point average roughness of 10 $\mu$m or less.

According to the second aspect of the invention, there is provided a gas sensor which comprises: (a) a hollow housing having a sealing shoulder formed on an inner wall thereof; (b) a sensor element having a length which includes a first and a second portion; (c) an insulating member disposed within the housing, retaining the sensor element therein hermetically, the insulating member having a sealing surface formed thereon; and (d) a metal sealing member interposed between the sealing shoulder of the housing and the sealing surface of the insulating member to hermetically define a first chamber in which the first portion of the sensor element is disposed and a second chamber in which the second portion of the sensor element is disposed. The metal sealing member has a Vickers hardness of 200 or less.

According to the third aspect of the invention, there is provided a gas sensor which comprises: (a) a hollow housing having a sealing shoulder formed on an inner wall thereof; (b) a sensor element having a length which includes a first and a second portion; (c) an insulating member disposed within the housing, retaining the sensor element therein hermetically, the insulating member having formed thereon a sealing surface having a ten-point average roughness of 10 $\mu$m or less; and (d) a metal sealing member interposed between the sealing shoulder of the housing and the sealing surface of the insulating member to hermetically define a first chamber in which the first portion of the sensor element is disposed and a second chamber in which the second portion of the sensor element is disposed.

In the preferred mode of the invention, the sealing surface of the insulating member is polished.

The sealing surface of the insulating member may alternatively be plated.

The insulating member is made of an alumina ceramic having an alumina purity of 90% or more.

According to the fourth aspect of the invention, there is provided a gas sensor which comprises: (a) a hollow housing having a sealing shoulder formed on an inner wall thereof; (b) a sensor element having a length which includes a first and a second portion; (c) an insulating member disposed within the housing, retaining the sensor element therein hermetically, the insulating member having a sealing surface formed thereon, the insulating member being made of an alumina ceramic having an alumina purity of 90% or more; and (d) a metal sealing member interposed between the sealing shoulder of the housing and the sealing surface of the insulating member to hermetically define a first chamber in which the first portion of the sensor element is disposed and a second chamber in which the second portion of the sensor element is disposed.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
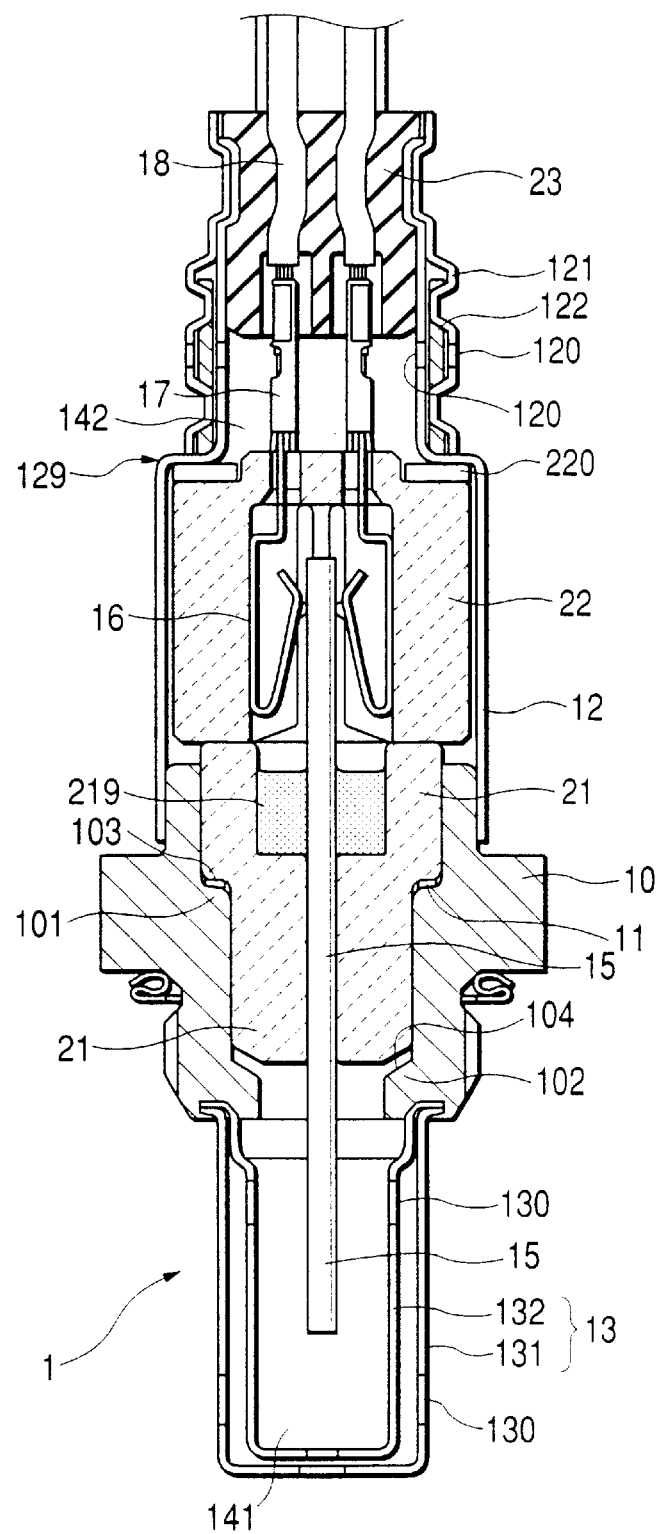
FIG. 1 is a longitudinal sectional view which shows a gas sensor according to the first embodiment of the invention.
Figure 2:
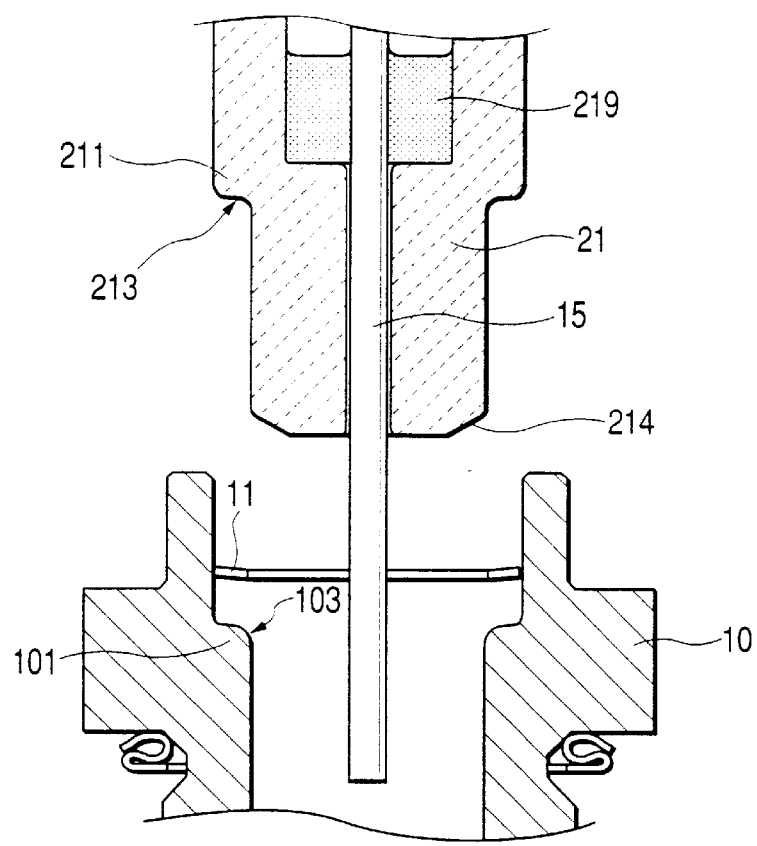
FIG. 2 is a partially sectional view which shows installation of a metal packing ring between an insulation porcelain and a housing.

Referring to the drawings, wherein like reference numbers refer to like parts in several views, particularly to FIGS. 1 and 2, there is shown a gas sensor 1 according to the first embodiment of the invention which may be employed in an air-fuel ratio control system for automotive vehicles to measure the concentration of a component such as NOx, CO, HC, or $O_2$ contained in exhaust gasses of the engine. The gas sensor 1 generally includes a sensor element 15, a first insulation porcelain 21, a second insulation porcelain 22, a hollow cylindrical housing 10, and an air cover 12. The sensor element 15 is made of a laminated plate. U.S. Pat. No. 5,573,650, issued on Nov. 12, 1996 to Fukaya et al. teaches a typical laminated sensor element, disclosure of which is incorporated herein by reference. The first insulation porcelain 21 is fitted within the housing 10 and holds therein the sensor element 15 through a glass sealing member 219. The second insulation porcelain 22 is mounted on the first insulation porcelain 21 and surrounds a base portion of the sensor element 15. The air cover 12 is installed at an end thereof on the housing 10 and surrounds the second insulation porcelain 22 to define an air chamber 142.

The second insulation porcelain 22 is made of a hollow cylindrical insulating member and has disposed therein four leads 16 (only two are shown for the simplicity of illustration) each of which is made of a wire folded elastically to make an electric contact at one end with an electrode terminal (not shown) formed on the sensor element 15. The leads 16 extend at the other end through holes formed in an end of the second insulation porcelain 22 and connect with four leads 18 through connectors 17, respectively, for transmission of sensor signals between the sensor element 15 and an external device and supply of electric power to a heater installed on the sensor element 15.

The gas sensor 1 also includes a protective cover assembly 13 consisting of an outer cover 131 and an inner cover 132. The protective cover assembly 13 is installed in a head of the housing 10 to define a gas chamber 141 into which a gas to be measured is admitted through gas holes 130 formed in the outer and inner covers 131 and 132.

The first insulation porcelain 21, as clearly shown in FIG. 2, has an annular shoulder 211 and a chamfered surface 214 formed on a head thereof. The chamfered surface 214 faces an inner shoulder 102, as shown in FIG. 1, formed in the housing 10 when the first insulation porcelain 21 is fitted within the housing 10. The shoulder 211 has a tapered surface 213 which is placed through a metal packing ring 11 on a seat surface 103 formed on an annular shoulder 101 on an inner wall of the housing 10. Specifically, a gap between the housing 10 and the first insulation porcelain 21 is sealed hermetically by the metal packing ring 11 to keep the air chamber 142 and the gas chamber 141 airtight. The seat surface 103 is inclined downward, as viewed in FIG. 1, to increase the degree of adhesion to the tapered surface 213 through the metal packing ring 11. The metal packing ring 11 is, as will be described later in detail, made of a pure nickel.

The air cover 12 is, as described above, fitted on the base end of the housing 10. An outer cover 121 is provided around the air cover 12 and staked or crimped to retain a water-repellent filter 122 on the periphery of the air cover 12. The air cover 12 and the outer cover 121 have formed therein air vents 120 through which air is admitted into the air chamber 142. The air cover 12, as clearly shown in FIG. 1, has a shoulder 129 to define a small-diameter portion and a large-diameter portion. A disc spring 220 is disposed between the shoulder 129 and an end of the second insulation porcelain 22 to elastically urge the second insulation porcelain 22 into constant engagement with the first insulation porcelain 21 to increase the degree of airtightness provided by the metal packing ring 11. An insulating holder 23 made of rubber is disposed inside the small-diameter portion of the air cover 12.

The sensor element 15, as described above, has a heater built therein which heats the sensor element 15 up to a temperature required for the sensor element 15 to be sensitive to a gas to be measured correctly. The sensor element 15 has formed thereon four electrode terminals two of which are used for outputting sensor signals and the others for supply of electric power to the heater. The electrode terminals are connected electrically with ends of the leads 16 in an illustrated manner, respectively. The leads 16 extend through the holes formed in the end wall of the second insulation porcelain 22 and are inserted into the connectors 17, respectively. The connectors 17 are coupled with the leads 18 retained in holes formed in the insulating holder 23. This structure is not essential part of this invention and known in the art, and explanation thereof in detail will be omitted here.

The first insulation porcelain 21 is, as described above, carried at the shoulder 211 on the shoulder 101 of the housing 10 through the metal packing ring 11. The metal packing ring 11 is made of a pure nickel of a 99% purity containing a small amount of impurities such as cobalt etc. The metal packing ring 11, therefore, has a highly dense surface which ensures a high degree of airtightness between the second insulation porcelain 21 and the housing 10. The metal packing ring 11 may alternatively be made of a nickel alloy, a titanium, a stainless steel, or a mixture of at least two of them (including a pure nickel). As the nickel alloy, a nickel-iron alloy, a nickel-copper alloy, a nickel-chrome alloy, a nickel-chrome-iron alloy, a nickel-molybdenum alloy, or a nickel base superheat-resistant alloy may be used. As the titanium, a pure titanium containing impurities of 1% or less such as that specified in one of Japanese Industrial Standard (JIS) Class 1 to Class 3 or one of ASTMG1 to ASTMG4 in U.S. is preferable. As the stainless steel, a martensitic, a ferrite, an austenitic, or an austenite-ferrite steel may be used. In a case where the gas sensor 1 is installed in an exhaust system of an automotive internal combustion engine to measure the concentration of a component such as NOx, CO, HC, or $O_2$ contained in exhaust gasses of the engine, the gas sensor 1 is subjected to intense heat and exposed to sulfur, therefore, a nickel or nickel alloy which has a high corrosion-resistance is preferable. The nickel or nickel alloy is inexpensive as compared with noble metals and allows the gas sensor 1 to be manufactured at low costs.

The metal packing ring 11 has a Vickers hardness of 200 Hv or less, preferably 150 Hv or less. In this embodiment, the hardness of the metal packing ring 11 is about 70 Hv. If the hardness of the metal packing ring 11 is more than 200 Hv, the shoulder 211 of the first insulation porcelain 21 is required to be pressed against the shoulder 101 of the housing 10 under high pressure to nip the metal packing ring 11 firmly, which may cause damage to the first insulation porcelain 21. If the first insulation porcelain 21 is made of a material capable of withstanding such a high pressure, it will result in an increase in manufacturing costs.

The metal packing ring 11 has a thickness of 0.1 mm or more (0.4 mm in this embodiment). If it is less than 0.1 mm, the metal packing ring 11 undergoes corrosion early, thus resulting in a decrease in service life thereof. Additionally, the machining of the metal packing ring 11 is difficult, thus resulting in an increase in manufacturing costs.

Figure 3:
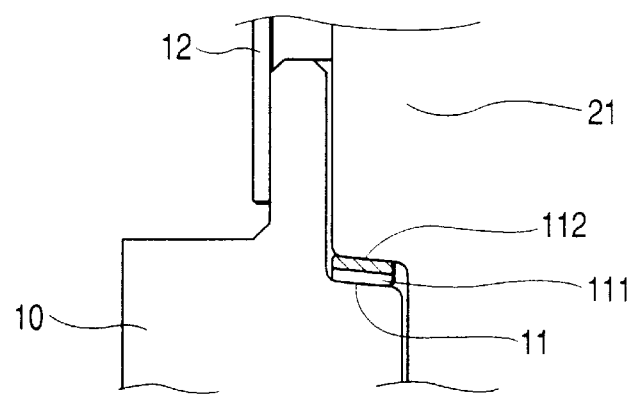
FIG. 3 is a partially sectional view which shows a metal packing ring according to the second embodiment of the invention.

FIG. 3 shows a second embodiment of the invention which is different from the first embodiment in that the metal packing ring 11 is made of two layers: a first layer 111 and a second layer 112. Other arrangements are identical, and explanation thereof in detail will be omitted here.

The first layer 111 and the second layer 112 are, as clearly shown in FIG. 3, laid to overlap each other. The first layer 111 is made of the same material as that of the metal packing ring 11 of the first embodiment. The second layer 112 is made of a material having a hardness lower than that of the first layer 111. For example, the first layer 111 is made of a pure nickel or a pure titanium. The second layer 112 is made of a stainless steel which is softer in mechanical property than the first layer 111. The reason for this will be discussed below. The housing 11 is usually made of an easy-to-machine metallic material which has a relatively lower hardness. The installation of the first insulation porcelain 21 in the housing 11 is accomplished by placing the first insulation porcelain 21 in which the sensor element 15 is fitted within the housing 11 through the metal packing ring 11, putting the second insulation porcelain 22 within which the leads 16 are disposed in the air cover 12 together with the disc spring 220, fitting the air cover 12 on the base portion of the housing 11, and welding the air cover 12 to the base portion of the housing 11 while pressing the air cover 12 downward, as viewed in FIG. 1, to have the tapered surface 213 of the first insulation porcelain 211 adhere to the seat surface 103 of the housing 11 through the metal packing ring 11. Therefore, the pressing the first insulation porcelain 21 against the housing 10 will cause the seat surface 103 of the housing 10 to be deformed, thereby increasing the degree of adhesion of the first layer 111 to the seat surface 103 of the housing 10. On the other hand, the first insulation porcelain 22 has a relatively higher hardness. The pressing the first insulation porcelain 21 against the housing 10 will, therefore, cause the second layer 112 softer than the first layer 111 to be deformed, thereby increasing the degree of adhesion of the second layer 112 to the tapered surface 213 of the first insulation porcelain 21.

Figure 4:
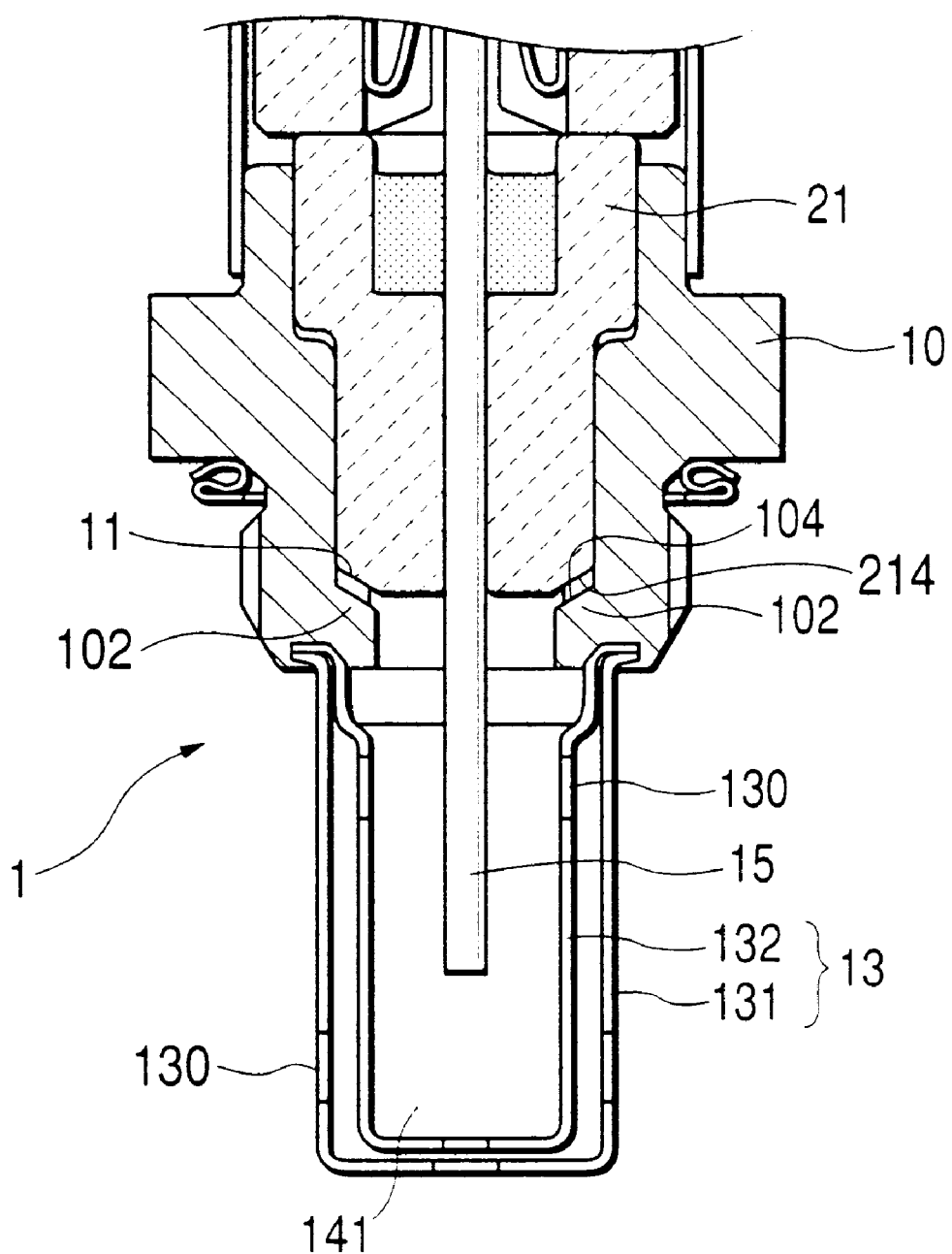
FIG. 4 is a partially longitudinal sectional view which shows a gas sensor according to the third embodiment of the invention.

FIG. 4 shows a gas sensor 1 according to the third embodiment of the invention.

The metal packing ring 11 is disposed between the chamfered surface 214 formed on the head of the first insulation porcelain 21 and the annular shoulder 102 formed on the inner wall of the housing 10, thereby keeping the air chamber 142 and the gas chamber 141 airtight. Other arrangement are identical with those in the first embodiment, and explanation thereof in detail will be omitted here.

In the above described first to third embodiments, the first insulation porcelain 21 may be made of an alumina ceramic having a 90% or more purity (preferably, 92% or more, more preferably, 95% or more). For instance, the first insulation porcelain 21 is made of an alumina ceramic of a purity of 98%. Further, it is preferable that the tapered surface 213 of the first insulation porcelain 21 on which the metallic packing ring 11 is placed have a relative roughness of 10 μm or less (preferably, 2 μm) as expressed by taking an average of ten samples (which is also referred to as a ten-point average), thereby providing a highly airtight seal between the first insulation porcelain 21 and the housing 10. The above roughness of the tapered surface 213 may be derived by polishing or plating with nickel, copper, or gold.

The first insulation porcelain 21 may alternatively be made of a silicon nitride or an aluminum nitride. The metal packing ring 11 may be made of a stainless steel plated with a nickel-copper.

Figure 6:
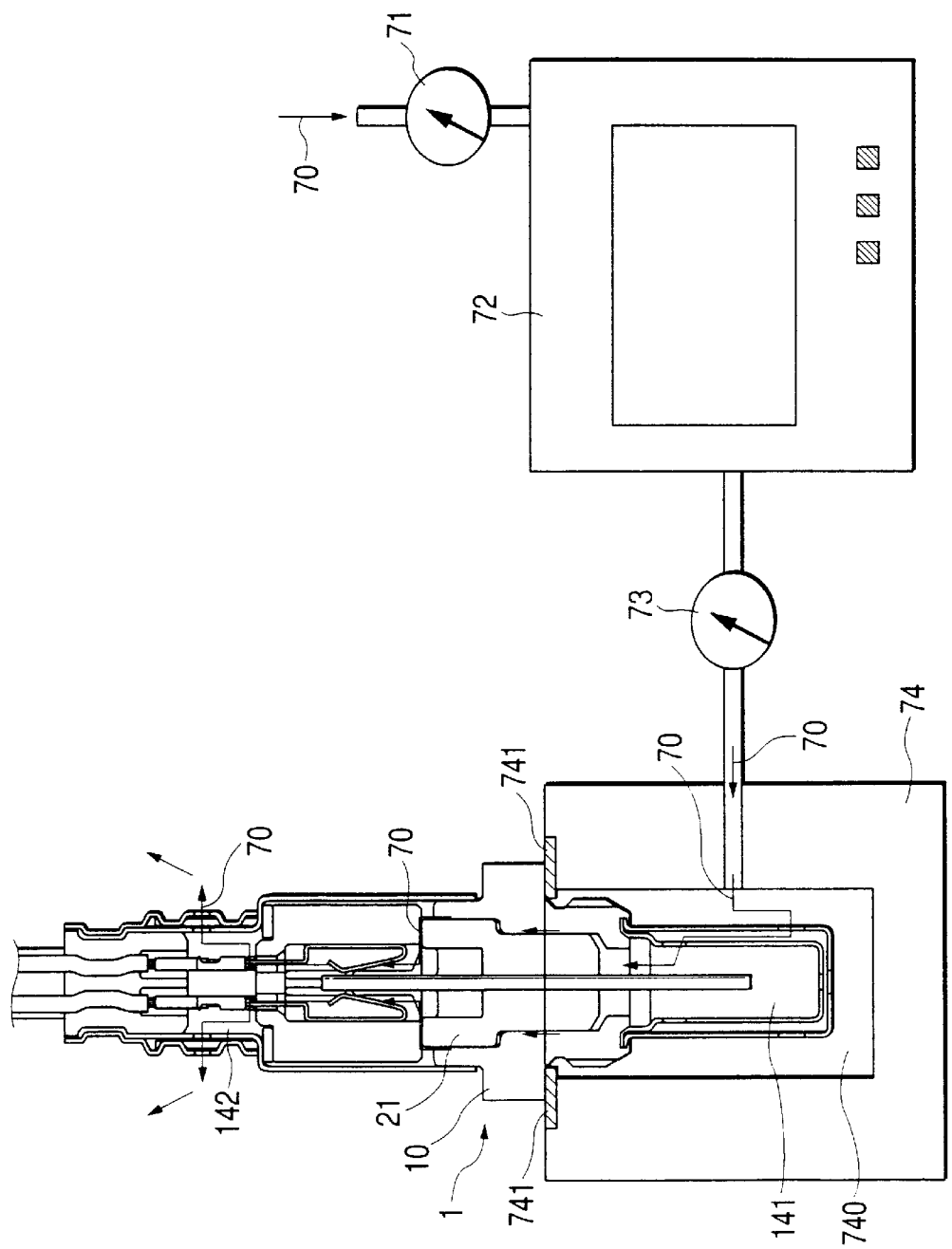
FIG. 6 is a view which shows a leakage test device.

Leakage tests were performed using a test device, as shown in FIG. 6, to find a relation between the roughness of the tapered surface 213 of the first insulation porcelain 21 and a gas leakage.

The test device includes a leakage measuring unit 72 equipped with an air regulator valve 71 and a gas sensor mount base 74. The leakage measuring unit 72 and the gas sensor mount base 74 are connected through a valve 73. The head of the gas sensor 1 is installed in an air cavity 740 of the gas sensor mount base 74 hermetically through a rubber seal 741.

Figure 5:
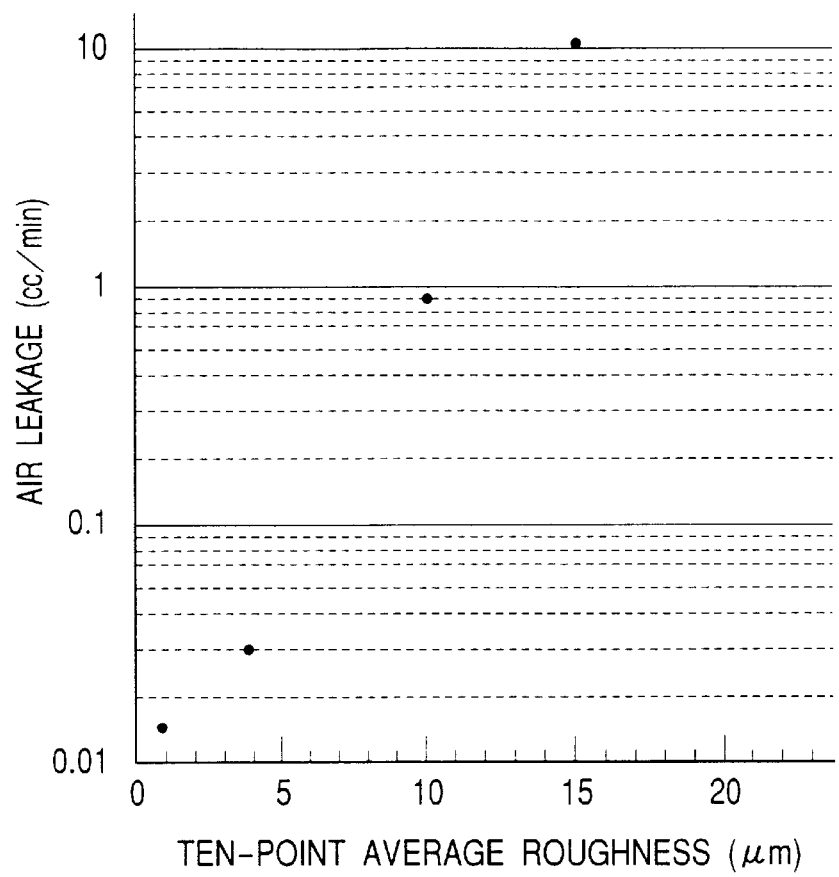
FIG. 5 is a graph which shows a relation between the roughness of a packing ring-mounted surface of a first insulation porcelain and a gas leakage.

10 minutes after the air 70 was supplied to the air cavity 740 at 4 atm., a drop in pressure in the air cavity 740 was measured to determine the amount of air (cc/min) leaking from the gas chamber 141 to the air chamber 142. This measurement was performed five times. The results of the measurements are shown in a graph of FIG. 5. The graph shows that when the ten-point average roughness of the tapered surface 213 is less than 10 μm, the amount of air leaking into the air chamber 142 is less than 1 cc/min., and when the ten-point average roughness is more than 15 μm, the air leakage exceeds an upper admissible limit of 10 cc/min.

Figure 7:
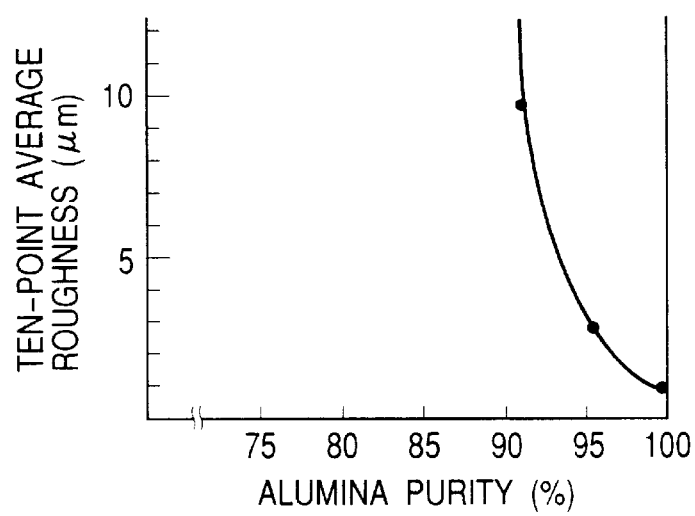
FIG. 7 is a graph which shows a relation between the roughness of a packing ring-mounted surface of a first insulation porcelain and an aluminum purity of the first insulation porcelain.

Further, the roughness of test pieces of the first insulation porcelain 21 made from alumina of different purities were measured to find a relation between the roughness of the tapered surface 213 and the alumina purity of the first insulation porcelain 21. The measurement of roughness of each of the test pieces was made three times over a length of 0.8 mm in accordance with JISB0601 using a needle whose tip angle is 90° and radius of curvature at the tip is 2 μm. The results of the measurements are shown in a graph of FIG. 7. The graph shows that when the purity of alumina exceeds 90%, the roughness of the tapered surface 213 of the first insulation porcelain 21 decreases greatly.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor comprising:
    a hollow housing having a sealing shoulder formed on an inner wall thereof;
    a sensor element having a length which includes a first and a second portion;
    an insulating member disposed within said housing, retaining said sensor element therein hermetically, said insulating member having formed thereon a sealing surface having a ten-point average roughness of 10 μm or less; and
    a metal sealing member interposed between the sealing shoulder of said housing and the sealing surface of said insulating member to hermetically define a first chamber in which the first portion of said sensor element is disposed and a second chamber in which the second portion of said sensor element is disposed.

2. A gas sensor as in claim 1 wherein said metal sealing member is made of at least one of a nickel, a nickel alloy, a titanium, and a stainless steel.

3. A gas sensor as set forth in claim 2, wherein the first chamber leads to the atmosphere, and the second chamber admits a gas to be measured thereinto.

4. A gas sensor as set forth in claim 3, further comprising an air cover installed on an end of said housing to define the first chamber therein.

5. A gas sensor as set forth in claim 2, wherein said metal sealing member has a Vickers hardness of 200 or less.

6. A gas sensor as set forth in claim 2, wherein said metal sealing member has a thickness of 0.1 mm or more.

7. A gas sensor as set forth in claim 2, wherein said metal sealing member comprises a first layer and a second layer, the first layer being in contact with the sealing shoulder of said housing, the second layer being in contact with the sealing surface of said insulating member and having a hardness lower than that of the first layer.

8. A gas sensor as in claim 7 wherein the second layer has a Vickers hardness of 150 or less.

9. A gas sensor as set forth in claim 2, wherein the sealing surface of said insulating member is tapered, and the sealing shoulder of said housing is so oriented as to adhere to the sealing surface of said insulating member through said metal sealing member.

10. A gas sensor as set forth in claim 2, wherein said insulating member is made of an alumina ceramic having an alumina purity of 90% or more.

11. A gas sensor as set forth in claim 10, wherein said metal sealing member has a Vickers hardness of 200 or less.

12. A gas sensor as in claim 1 wherein said metal sealing member has a Vickers hardness of 200 or less.

13. A gas sensor as set forth in claim 1, wherein the sealing surface of said insulating member is plated.

14. A gas sensor as set forth in claim 1, wherein said insulating member is made of an alumina ceramic having an alumina purity of 90% or more.

15. A gas sensor as in claim 1 wherein the sensor element comprises a laminated sensor element.

16. A gas sensor as in claim 1 wherein the amount of the ten-point average roughness of the sealing surface of the insulating member is based on the purity of the insulating member.

* * * * *